United States Patent
Kulkarni et al.

(10) Patent No.: US 6,365,208 B1
(45) Date of Patent: *Apr. 2, 2002

(54) STABLE LACTASE TABLETS

(75) Inventors: Sunanda R. Kulkarni, N. Wales, PA (US); Robert T. McFadden, Congers, NY (US); David H. Rogers; James T. Walter, Jr., both of Ambler, PA (US)

(73) Assignee: McNeil-PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/943,827

(22) Filed: Oct. 3, 1997

Related U.S. Application Data

(63) Continuation of application No. 08/496,818, filed on Jun. 29, 1995, now abandoned.

(51) Int. Cl.[7] .................................................. A23L 1/28
(52) U.S. Cl. ........................... 426/61; 426/63; 426/285; 426/573; 435/188
(58) Field of Search ............................ 426/61, 63, 573, 426/285; 424/464, 465, 94.61; 435/179, 188, 200, 207

(56) References Cited

U.S. PATENT DOCUMENTS

| | | | | |
|---|---|---|---|---|
| 3,718,739 A | * | 2/1973 | Cayle ....................... 424/94.61 |
| 3,954,979 A | | 5/1976 | Bowman .................... 424/195 |
| 4,034,035 A | | 7/1977 | Schwartz et al. ............. 264/77 |
| 4,079,125 A | * | 3/1978 | Sipos ......................... 424/480 |
| 6,057,139 A | * | 5/2000 | Kulkarni et al. ............. 435/188 |

* cited by examiner

Primary Examiner—Leslie Wong

(57) ABSTRACT

There is a formulation having improved chemical stability containing:

a) from about 1% to about 20% by weight of a combination of lactase and cutting agent where said combination has from 0 to about 4 parts by weight cutting agent for each part by weight lactase;

b) from about 1% to about 98% by weight of microcrystalline cellulose;

c) from about 0% to about 97% by weight of mannitol; and d) an effective amount of lubricant to aid compression.

11 Claims, No Drawings

STABLE LACTASE TABLETS

This is a continuation of application Ser. No. 08/496,818, filed Jun. 29, 1995, now abandoned.

The present invention relates to lactase tablets having improved chemical stability. More particularly, the present invention relates to lactase tablets containing lactase, microcrystalline cellulose, lubricant and mannitol.

BACKGROUND OF THE INVENTION

Lactose, or milk sugar, is a disaccharide carbohydrate which is hydrolyzed during the digestive process to glucose and galactose. This hydrolysis is catalyzed by the enzyme lactase, or beta-galactosidase. Although this enzyme is normally present in the intestinal juices and mucosa, investigations have shown that a significant portion of the population is lactose intolerant or lactase deficient. Consequently, there has been a great demand for a dietary supplement of lactose-hydrolyzing lactase enzymes in lactose intolerant individuals.

Commercially available tablets containing lactase have been observed to have an undesireably short shelf-life. Generally, it is desirable to have a shelf-life beyond about 24 months.

Shelf-life, as used herein for a lactase tablet product, is the time it takes for the lower 95% confidence interval of the product's potentcy plotted versus time to fall below a predetermined lower specification limit. Thus, it can be seen that shelf-life is a function of lactase content uniformity in the tablets and the inherent lactase chemical stability. It is an object of the present invention to formulate a lactase containing tablet composition having improved chemical stability.

SUMMARY OF THE INVENTION

Breifly, there is provided by the present invention a lactase tablet formulation comprising:
a) from about 1% to about 20% by weight of a combination of lactase and cutting agent where said combination has from 0 to about 4 parts by weight cutting agent for each part by weight lactase;
b) from about 1% to about 98% by weight of microcrystalline cellulose;
c) from about 0% to about 97% by weight of mannitol; and
d) an effective amount of lubricant to aid compression.

DETAILED DESCRIPTION OF THE INVENTION

Lactose hydrolyzing lactase enzymes are known to be produced by various yeasts, bacteria and fungi. Among the organisms heretofore disclosed as useful for this purpose are yeasts, such as, *Saccharomyces fragilis, Torula cremoris* and *Torula utilis*, bacteria, such as, Escherichia coli and *Lactobacillus bulgaricus*, fungi, such as, *Aspergillus oryzae, Aspergillus flavus* and *Aspergillus niger*, and various other micro-organisms, such as, those described in U.S. Pat. Nos. 2,681,858, 2,781,266 and 2,809,113. The lactase enzyme preparations produced by these organisms generally have pH optimums on the alkaline side or in the weakly acid pH range of about 5–7. Yeasts, which are the primary source of commercial lactases, are known to produce lactases having pH optimums of about 7. Most of these conventional lactase enzyme preparations contain other proteins in admixture therewith. When lactase is referred to herein, it is such an admixture that is referred to.

As seen, lactase enzymes are commercially produced as biological products which have a variability in potency from batch to batch that requires adjustment with a cutting agent in order to produce a uniform commercial product. Cutting agent is added to the lactase enzyme product and the amount is adjusted from batch to batch to produce a lactase enzyme product of the target potentcy. Cutting agents may be selected from any inert pharmaceutical excipient, including, sugars, starches, cellulose and inorganic salts. The amount or even the absence of the cutting agent herein is not critical to the present invention. Of course, it is desireable in the practice of the present invention that the lactase be in a readily available and convenient form of known potentcy for addition to the formulation. Suitable cutting agents include dextrose, mannitol, calcium phosphate, sodium citrate and microcrystalline cellulose.

Suitable lactase for use herein include, a lactase isolated from *Saccharomyces lactis*, by Gist-Brocade in Delft, Holland, and sold by Enzyme Development Corporation, New York, N.Y.; a lactase from *Aspergillus oryzae*, Lactase Y-400, produced by K. K. Yakult Honsha; a lactase from *Aspergillus oryzae*, Plexazym LA 1, produced by Roehm GmbH; a lactase from *Aspergillus oryzae*, produced by Shinnihon Kagaku Kogyo Co.; a lactase from *Kluyveromyces fragilis* produced by Sturges Enzymes, Selby, North Yorkshire, England; a lactase from *Aspergillus oryzae*, Takamine lactase, produced by Miles Laboratories, Inc., Elkhart, Ind.; and a lactase from *Kluyveromyces fragilis* produced by Novo Enzymes, Bagsvaerd, Denmark. These suppliers and others offer, generally, lactase, including a cutting agent, having a potentcy of between 14,000 and 100,000 FCC lactase units/gram. Preferrably the combination of lactase and cutting agent is present in the lactase tablet formulation in an amount of from about 5% to about 15% by weight and said combination has from about 0 to about 3 parts by weight cutting agent and more preferably from about 0.5 to about 2 parts by weight for each part by weight lactase. A preferred lactase for use herein is from *Aspergillus oryzae* produced by Amano Pharmaceutical Company, LTD, under the tradename Lactase F "Amano" 100. This preferred lactase contains, on a weight basis, about 50% a mixture containing sodium citrate and dextrose and the balance of lactase and has a potentcy of 100,000 FCC lactase units/gram.

Microcrystalline cellulose is manufactured by the controlled hydrolysis of alpha-cellulose, obtained as a pulp from fibrous plant materials, with dilute mineral acid solutions. Following hydrolysis, the hydrocellulose is purified by filtration and the aqueous slurry is spray dried to form dry, porous particles of a broad size distribution. Suitable microcrystalline cellulose will have an average particle size of from about 20 to about 200 $\mu$m. Microcrystalline cellulose is available from several suppliers. Suitable microcrystalline cellulose includes Avicel PH 101, Avicel PH 102, Avicel PH 103, Avicel PH 105 and Avicel PH 200, manufactured by FMC Corporation. Preferably the microcrystalline cellulose is present in the lactase tablet formulation in an amount of from about 10% to about 85% by weight and more preferably in an amount of from about 25% to about 70% by weight.

Mannitol is a well known sweetner and excipient in pharmaceutical preparations. The mannitol should be ground to have an average particle size of between about 50 $\mu$m and about 500 $\mu$m prior to formulating. Preferably the mannitol is present in the lactase tablet formulation in an amount of from about 15% to about 80% by weight and more preferably in an amount of from about 25% to about 70% by weight.

Examples of the lubricants include magnesium stearate, talc, polyethylene glycol, silica and hardened vegetable oils. The preferred lubricant is magnesium stearate. Preferably, the lubricant is present in the lactase tablet formulation in an amount of from about 0.25% to about 6% and most preferably from about 0.5% to about 4% by weight.

In preparing the lactase tablets of this invention, the active lactase is simply mixed with the other ingredients and pressed into tablets by standard techniques. To achieve the benefit of the invention herein, it is not critical that any order of mixing be observed. However, it is the practice in formulating tablets, that the magnesium stearate is added as a last ingredient before compression. Also, it is preferred in making the tablets herein that the lactase is first thoroughly mixed with the microcrystalline cellulose before mixing with the mannitol.

The quantity of lactase enzyme administered in a single oral dosage can vary within wide limits. This quantity will depend on factors which include the lactase activity of the lactase enzyme, the magnitude of the lactase deficiency or lactose intolerance in the particular individual requiring the dietary supplement of lactase and the dietary habits of the individual. As a general matter, the affected individual will become accustomed to estimating a required dose based on the particular facts and experience.

Ideally, the lactase tablets herein should contain sufficient lactase to satisfy the dosage requirement of most individuals requiring the dietary supplement of lactase in most situations. Alternatively, the lactase tablets herein should contain a fraction of such a dose so that the gamut of affected individuals can closely match their dosage requirements with the administration of one, two or three tablets. In the first case, a tablet herein might contain 9000 FCC lactase unit/tablet and, in the second case, 3000 FCC lactase unit/tablet.

The following examples are intended to illustrate the invention herein and are in no way intended to be limiting:

EXAMPLE 1

The lactase employed in each blend of Example 1 was Lactase F "Amano" 100, as described above, and the microcrystalline cellulose was Avicel PH 102, with an average particle size of 100 $\mu$m. All ingredients except the lactase were delumped by screening through a hand screen. The amount of each ingredient for each blend is given in Table 1.

blend A

The lactase, microcrystalline cellulose, and mannitol were charged to a 1 ft³ twin shell blender and blended for 15 minutes. Magnesium stearate was added to the blend and blended for 5 additional minutes. Tablets were compressed on a rotary tablet press at the target weight.

blend B

The lactase enzyme and dextrate were charged to a 16 quart twin shell blender and blended for 15 minutes. The remaining components were added to the blend, less the hydrogenated vegetable oil, and blended for an additional 10 minutes. Hydrogenated vegetable oil was added to the blend and blended for 10 additional minutes. Tablets were compressed on a rotary tablet press at the target weight.

blend C

A commercial formula is tested and the components are disclosed based on labeling.

blend D

The microcrystalline cellulose and lactase were combined in a gravity blender and blended for 15 minutes, 30 ft³, 14–16 rpm. The mannitol was delumped by passing it through a #10 screen, combined with the microcrystalline cellulose/lactase blend and the resulting combination was blended an additional 10 minutes. The magnesium stearate was delumped by passing it through a #20 mesh screen, combined with the mannitol/microcrystalline cellulose/lactase blend and the resulting combination was blended an additional 10 minutes. Tablets were compressed on a rotary tablet press at the target weight.

TABLE 1

| ingredients\blend | A | B | C | D |
| --- | --- | --- | --- | --- |
| lactase | 12.0 | 9.6 | x | 9.6 |
| microcrystalline cellulose | 30.0 | 8.6 | x | 30.0 |
| mannitol | 57.0 | | | 59.4 |
| dextrates | | 38.7 | x | |
| pregelatized starch | | 4.2 | x | |
| dibasic calcium phosphate | | 28.4 | x | |
| croscarmellose sodium | | 6.3 | x | |
| hydrogenated vegetable oil | | 4.2 | x | |
| magnesium stearate | 1.0 | | | 1.0 |

Bottles of 50 tablets of blends A–D were stored at 35° C. and tested for active lactase content at 0, 1, 3 and 6 months. The results are reported in Table 2 as percent of initial lactase activity. Lactase activity was determined by an adaptation of the method described in the *Food Chemicals Codex*, National Academy Press, 1981, pages 491–492, using o-nitrophenyl-β-D-galactopyranoside as substrate incubated at pH 4.5 and 37° C. Analyses were performed as described with the following modifications. The standard preparation was changed from the published 1% sodium bicarbonate solution to a solution prepared in 1% sodium carbonate in order to match the composition of the final stopped reaction mixture. A single standard of 0.14 mM o-nitrophenyl was used. The assay volumes were reduced by half (2.0 mL of substrate solution and 0.5 mL of test solution) in order to perform the final dilution in the orginal test tube.

TABLE 2

| months\blend | A | B | C | D |
| --- | --- | --- | --- | --- |
| 0 | 100 | 100 | 100 | 100 |
| 1 | 103 | 90 | 98 | 97 |
| 3 | 88 | 73 | 56 | 89 |
| 6 | 94 | 75 | 27 | 81 |

What is claimed is:

1. A formulation comprising:
   a) from about 9.6 to about 12 weight percent lactase mixture; said lactase mixture contains about 50% lactase;
   b) about 30 weight percent microcrystalline cellulose;
   c) from about 57 to about 59.4 weight percent mannitol;
   d) an effective amount of lubricant to aid compression;
   wherein about at least about 81% of the initial lactase is present after storage after 6 months at 35° C.

2. The formulation of claim 1 wherein the lubricant is magnesium stearate.

3. The formulation of claim 1 which is formed into a tablet.

4. The formulation of claim 3 wherein the tablet contains 3000 FCC lactase unit/tablet.

5. The formulation of claim 3 wherein the tablet contains 9000 FCC lactase unit/tablet.

6. The formulation of claim 1 wherein at least about 94% of the initial lactase is present after storage after 6 months at 35° C.

7. A formulation comprising:
   a) from about 3000 to about 9000 FCC lactase units;
   b) about 30 weight percent microcrystalline cellulose;
   c) from about 57 to about 59.4 weight percent mannitol.

8. The formulation of claim 7 further comprising an effective amount of lubricant to form a tablet.

9. The formulation of claim 7 wherein the least about 81% of the initial lactase is present after storage after 6 months at 35° C.

10. The formulation of claim 8 wherein the lubricant is selected from the group consisting of magnesium stearate, talc, polyethylene glycol, silica and hardened vegetable oil.

11. The formulation of claim 8 wherein the lubricant is provided in an amount from about 0.25 to about 6 weight percent.

* * * * *